United States Patent [19]

Kurimoto et al.

[11] Patent Number: 5,700,752

[45] Date of Patent: Dec. 23, 1997

[54] CATALYST FOR PRODUCTION OF UNSATURATED ALDEHYDE AND UNSATURATED CARBOXYLIC ACID AND METHOD FOR PRODUCTION OF UNSATURATED ALDEHYDE AND UNSATURATED CARBOXYLIC ACID BY THE USE OF THE CATALYST

[75] Inventors: Ikuo Kurimoto; Tatsuya Kawajiri; Hideo Onodera; Michio Tanimoto; Yukio Aoki, all of Hyogo, Japan

[73] Assignee: Nippon Shokubai Co. Ltd., Osaka-fu, Japan

[21] Appl. No.: 456,062

[22] Filed: May 31, 1995

[30] Foreign Application Priority Data

May 31, 1994 [JP] Japan ................... 6-118229

[51] Int. Cl.$^6$ ............. B01J 23/25; B01J 23/30; B01J 23/31
[52] U.S. Cl. ............. 502/311; 503/305; 503/313; 503/321; 568/477
[58] Field of Search ............. 502/305, 311, 502/313, 321; 568/479

[56] References Cited

U.S. PATENT DOCUMENTS

| | | | |
|---|---|---|---|
| 4,918,041 | 4/1990 | Hollstein et al. | 502/217 |
| 5,198,581 | 3/1993 | Kawajiri et al. | 562/546 |

FOREIGN PATENT DOCUMENTS

| | | |
|---|---|---|
| 0456837 | 6/1990 | European Pat. Off. . |
| 5013308 | 6/1973 | Japan . |
| 5047915 | 8/1973 | Japan . |
| 5940056 | 8/1979 | Japan . |
| 596181 | 8/1979 | Japan . |
| 6456634 | 8/1987 | Japan . |
| 01288339 | 5/1988 | Japan . |
| 05293375 | 4/1992 | Japan . |

OTHER PUBLICATIONS

European Search Report, EP 95 10 8273, Nov. 3, 1995.
Recent Progess in Solid Superacid, Applied Catalysis, 61 (1990) 1–25 no month.
Copy of Taiwanese Official Action and Applicants' response. Jun. 1995.

*Primary Examiner*—Elizabeth D. Wood
*Assistant Examiner*—Alexander G. Ghyka
*Attorney, Agent, or Firm*—Omri M. Behr, Esq.

[57] ABSTRACT

A catalyst for the production of unsaturated aldehyde and unsaturated carboxylic acid by the vapor-phase catalytic oxidation of at least one compound selected from the group consisting of propylene, isobutylene, t-butanol and methyl-t-butyl ether and a method for the production of unsaturated aldehyde and unsaturated carboxylic acid by the use of this catalyst are provided. The catalyst of this invention comprises (A) a catalyst having Mo, Bi and Fe as essential components and used for the production of unsaturated aldehyde and unsaturated carboxylic acid by vapor-phase catalytic oxidation of propylene, isobutylene, t-butanol and/or methyl-t-butyl ether and (B) a solid acid having acid strength (Ho) of not more than −11.93. Since this catalyst excels in catalytic activity and service life, it allows unsaturated aldehyde and unsaturated carboxylic acid to be produced stably at a high yield for a long time.

10 Claims, No Drawings

CATALYST FOR PRODUCTION OF UNSATURATED ALDEHYDE AND UNSATURATED CARBOXYLIC ACID AND METHOD FOR PRODUCTION OF UNSATURATED ALDEHYDE AND UNSATURATED CARBOXYLIC ACID BY THE USE OF THE CATALYST

BACKGROUND OF THE INVENTION

1. Field of the Invention

This invention relates to a catalyst for the production of unsaturated aldehyde and unsaturated carboxylic acid and a method for the production of unsaturated aldehyde and unsaturated carboxylic acid by the use of this catalyst. More particularly, it relates to a catalyst for producing unsaturated aldehyde and unsaturated carboxylic acid stably at a high yield for a long time by the vapor-phase catalytic oxidation of at least one compound selected from the group consisting of propylene, isobutylene, t-butanol and methyl-t-butyl ether and to a method for the production of unsaturated aldehyde and unsaturated carboxylic acid by the use of this catalyst.

2. Description of the Prior Art

Various improved catalysts have been proposed for the efficient production of unsaturated aldehyde and unsaturated carboxylic acid by the vapor-phase catalytic oxidation reaction of propylene or isobutylene, for example. For example, JP-A-50-13,308 and JP-A-50-47,915 disclose a catalyst having Mo, Bi, Fe, Sb and Ni and at least one element selected among K, Rb and Cs as essential components, and JP-A-64-56,634 discloses a catalyst having Mo, Bi and Fe and at least one element selected among Ni and Co as essential components. As shown from the disclosures mentioned above, most of the proposed catalysts have molybdenum, bismuth and iron as main components thereof.

The problem confronting these catalysts resides in the fact that they are considered to be still deficient not only in the yield of unsaturated aldehyde and unsaturated carboxylic acid but also in the service life of the catalysts. Further, the fact that molybdenum contained in the catalyst is easily sublimed induces an irreversible degradation of catalytic activity. The oxidation reaction mentioned above is an extremely exothermic reaction. With due consideration of the prominent subliming of molybdenum in a catalytic layer, particularly a local abnormal high-temperature zone so called as "hot spot", the use of a catalyst at a high temperature must be avoided to the utmost. A catalyst having a high activity and manifesting the function thereof stably for a long time has been longed for. In particular, in a high-load operation aimed at a high productivity, in the light of the larger amount of accumulated heat in a hot spot in combination with the longer time of using a catalyst at a high temperature because of a more rapid degradation thereof as compared to that in the general reaction, a catalyst which has a high activity and manifests the function thereof stably for a long period is considered to be indispensable.

Solid acids whose magnitudes of acid strength (Ho) (hereinafter referred to simply as "acid strength" or occasionally as "Ho") are not more than −11.93 are generally called as solid super acids as introduced in detail in "SHOKUBAI", Vol. 31 No 7 (1989), pp 512 through 518, for example. According to the literature, the super acid is defined as an acid possessing acidity stronger than that of 100% sulfuric acid (Ho$\leq$−11.93) and is reported to be usable under more moderate conditions than the ordinary acid catalysts in such reactions as decomposition, isomerization, alkylation, polymerization, acylation, dehydration, and dehydrogenation of hydrocarbon which are referred to as acid catalytic reactions. The fact that this super acid, particularly when combined with a molybdenum-bismuth-iron type catalyst, is effective in inducing the vapor-phase catalytic oxidation reaction for producing unsaturated aldehyde and unsaturated carboxylic acid from propylene and isobutylene, for example, has not been known at all to the art.

One object of this invention, therefore, is to provide a catalyst for producing unsaturated aldehyde and unsaturated carboxylic acid at a high yield.

Another object of this invention is to provide a catalyst for the production of unsaturated aldehyde and unsaturated carboxylic acid which excels in terms of service life and permits the stable operation of the catalytic reaction for a long time.

Still another object of this invention is to provide a catalyst for the production of unsaturated aldehyde and unsaturated carboxylic acid which, even in a high-load operation aimed at high productivity, permits this operation to proceed stably for a long time.

Yet another object of this invention is to provide a method for producing unsaturated aldehyde and unsaturated carboxylic acid efficiently by the use of the catalyst just mentioned above.

SUMMARY OF THE INVENTION

The objects mentioned above are accomplished by a catalyst for producing unsaturated aldehyde and unsaturated carboxylic acid by the oxidation of at least one compound selected from the group consisting of propylene, isobutylene, t-butanol and methyl-t-butyl ether in a vapor phase with a molecular oxygen-containing gas, which catalyst comprises (A) a composite oxide having molybdenum, bismuth and iron as essential components and adapted for the production of unsaturated aldehyde and unsaturated carboxylic acid by the vapor-phase catalytic oxidation of propylene, isobutylene, t-butanol and/or methyl-t-butyl ether and (B) a solid acid having acid strength (Ho) of not more than −11.93 (Ho$\leq$−11.93). These objects are further accomplished, in the vapor-phase catalytic oxidation reaction for producing unsaturated aldehyde and unsaturated carboxylic acid by the oxidation of at least one compound selected from the group consisting of propylene, isobutylene, t-butanol and methyl-t-butyl ether in the vapor phase with the molecular oxygen-containing gas, by a method for the production of unsaturated aldehyde and unsaturated carboxylic acid which effects the reaction in the presence of the catalyst mentioned above.

The present inventors have learnt that a catalyst composition which combines a composite oxide having molybdenum, bismuth and iron as essential components with a solid acid having acid strength of not more than −11.93 possesses high activity as a catalyst for the production of unsaturated aldehyde and unsaturated carboxylic acid and excels in stability of a catalyst and that the objects mentioned above can be attained by using this catalyst composition. This invention have been perfected on the basis of this knowledge.

Since the catalyst of this invention maintains high activity, it aids in the production of unsaturated aldehyde and unsaturated carboxylic acid at a high yield.

Since the catalyst of this invention excels in terms of service life and maintains this outstanding quality for a long time, it permits unsaturated aldehyde and unsaturated carboxylic acid to be produced stably for a long time. Even after a protracted use, this catalyst can continue the reaction for the production of unsaturated aldehyde and unsaturated carboxylic acid at the same degree of yield as during the initial stage of the reaction without appreciably increasing the reaction temperature.

Since the catalyst of this invention exhibits high activity even at low temperatures, it aids in effecting the reaction at the same degree of yield at reaction temperatures lower than those necessary for the conventional methods.

Since the catalyst of this invention suffers no degradation of catalytic property even under high-load operation conditions aimed at a high productivity, it permits unsaturated aldehyde and unsaturated carboxylic acid to be produced stably with high operational efficiency for a long time.

By the method of this invention, unsaturated aldehyde and unsaturated carboxylic acid can be produced efficiently and advantageously on a commercial scale.

DESCRIPTION OF THE PREFERRED EMBODIMENT

Now, this invention will be described in detail below.

Component (A):

As the component (A), any of the well-known composite oxide catalysts which have molybdenum, bismuth and iron as essential components and are used for producing unsaturated aldehyde and unsaturated carboxylic acid by the vapor-phase catalytic oxidation of at least one compound selected from the group consisting of propylene, isobutylene, t-butanol and methyl-t-butyl ether can be used. In these catalysts, those catalysts which are represented by the following general formula (1):

$$Mo_aW_bBi_cFe_dA_eB_fC_gD_hE_iO_x$$

(wherein Mo is molybdenum, W is tungsten, Bi is bismuth, Fe is iron, A is at least one element selected from the group consisting of nickel and cobalt, B is at least one element selected from the group consisting of alkali metals and thallium, C is at least one element selected among alkaline earth metals, D is at least one element selected from the group consisting of phosphorus, tellurium, antimony, tin, cerium, lead, niobium, manganese, arsenic and zinc, E is at least one element selected from the group consisting of silicon, aluminum, titanium and zirconium, and O is oxygen, and a, b, c, d, e, f, g, h, i, and x are atomic ratios respectively of Mo, W, Bi, Fe, A, B, C, D, E, and O such that b is a numeral in the range of 0 to 10, preferably 0.5 to 10, c in the range of 0.1 to 10, preferably 0.2 to 6, d in the range of 0.1 to 20, preferably 0.2 to 10, e in the range of 2 to 20, preferably 3 to 15, f in the range of 0.001 to 10, preferably 0.002 to 5, g in the range of 0 to 10, preferably 0 to 5, h in the range of 0 to 4, preferably 0 to 2, i in the range of 0 to 30, preferably 0 to 15, and x is a numeral to be determined by the oxidized states of the elements when a is fixed at 12), are advantageously used.

These catalysts are not discriminated on account of their methods of preparation. They may be prepared by any of the well-known methods. The compound containing the relevant elemental component as a starting material is not particularly limited by its kind. Any of the oxides which contain the relevant elemental component or the compounds which produce the oxides when calcined can be used. As typical examples of the compound which produces the oxides when calcined, hydroxides, metallic acids, nitrates, carbonates, ammonium salts, acetates, and formates may be cited. The compound which contains two or more elemental components cited above is likewise usable.

Generally, the composite oxide of the component (A) is obtained by suitably dissolving compounds containing relevant elemental components as a starting material in required amounts as in an aqueous medium, for example, heating and stirring them in the medium, then evaporating the resultant liquid mixture to dryness, and further pulverizing the resultant dry mixture when necessary.

Component (B):

The solid super acid as the component (B) is known, as remarked in the literature "SHOKUBAI" mentioned above, in two kinds, sulfuric acid-carried super acid and oxide-carried super acid. As typical examples of these kinds, the following super acids (1) through (7) may be cited.

(1) Super acids of $SO_4$/oxide of a metal of Group IV in the Periodic Table of Elements:

In the metals of Group IV in the Periodic Table of Elements, zirconium, titanium, tin, and hafnium are favorably used. These metals may be used in the form of a mixture of two or more members. As typical examples of the super acid of this category, $SL_4$/zirconium oxide, $BO_4$/titanium oxide, $BO_4$/tin oxide, and $SO_4$/hafnium oxide may be cited. They are represented as $SO_4/ZrO_2$, $SO_4/TiO_2$, $SO_4/Sn_{O2}$, and $SO_4/HfO_2$ respectively. These super acids are dealt with in such publications as "Advances in Catalysis", Vol. 37, pp. 182–191 (1990) and "Applied Catalysis", Vol. 61, pp. 1 to 25 (1990) besides "SHOKUBAI" mentioned above.

The method for the preparation of these super acids will be explained below with respect to zirconium as an example. The $SO_4$/zirconium oxide super acid is obtained by combining zirconium hydroxide or amorphous zirconium oxide with a sulfate ion-containing solution such as, for example, sulfuric acid or an aqueous sulfuric acid solution, then removing an excess of the sulfate ion-containing solution, subsequently drying the resultant wet mixture, and calcining the dry mixture in the atmosphere of an inert gas such as air or nitrogen gas at a temperature in the range of 3500° to 800° C., preferably 400° to 700° C. for a period in the approximate range of 1 to 10 hours, preferably 2 to 8 hours. The super acid of other metal can be prepared by following this procedure while using the hydroxide or amorphous oxide of the metal instead.

It is generally held that, in the super acid which is obtained as described above, the sulfate ion ($SO_4^{2-}$) is bound to or carried on a metal oxide. This super acid is expressed as $SO_4$/metal oxide ($MeO_x$) in the publications "SHOKUBAI" and "Advances in Catalysis" mentioned above. The super acids which are used in the present invention, therefore, will be expressed after this manner.

(2) $SO_4$/iron oxide super acid:

This super acid is expressed as $SO_4/Fe_2O_3$ and is dealt with in the publications of "SHOKUBAI" and "Advances in Catalysis" and in "Chemistry Letters", pp. 1259 to 1260 (1979) as well.

This super acid is obtained by combining the hydroxide or amorphous oxide of iron with a sulfate ion-containing solution such as, for example, sulfuric acid or an aqueous sulfuric acid solution, then removing an excess of the sulfate ion-containing solution from the resultant liquid mixture, then drying the wet mixture, and calcining the dry mixture in the atmosphere of an inert gas such as air or nitrogen gas at a temperature in the range of 350° to 800° C., preferably 400° to 650° C. for a period in the approximate range of 1 to 10 hours, preferably 2 to 8 hours.

(3) $SO_4$/silicon oxide super acid:

This super acid is expressed as $SO_4/SiO_2$ and dealt with in the publications of "SHOKUBAI" and "Advances in Catalysis" mentioned above.

This super acid is obtained by combining silica gel with a sulfur-containing compound such as, for example, sulfuryl chloride, then drying the resultant liquid mixture, and subsequently calcining the dry mixture in the atmosphere of an inert gas such as air or nitrogen gas at a temperature in the range of 300° to 600 ° C., preferably 350° to 500 ° C. for a period in the approximate range of 1 to 10 hours, preferably 2 to 8 hours.

(4) $SO_4$/aluminum oxide super acid:

This super acid is expressed as $SO_4/Al_2O_3$ and dealt with in the publications of "SHOKUBAI" and "Advances in Catalysis" mentioned above.

This super acid is obtained by combining γ-alumina or aluminum hydroxide with a sulfate ion-containing solution such as, for example, sulfuric acid or an aqueous sulfuric acid solution, removing an excess of the sulfate ion-containing solution, then drying the resultant wet mixture, and subsequently calcining the dry mixture in the atmosphere of an inert gas such as air or nitrogen gas at a temperature in the range of 350° to 800 ° C. preferably 400° to 700 ° C. for a period in the approximate range of 1 to 10 hours, preferably 2 to 8 hours.

(5) Tungsten oxide, molybdenum oxide, or tungsten-molybdenum composite oxide/zirconium oxide super acid:

These super acids are expressed as $WO_3/ZrO_2$, $MoO_3/ZrO_2$, and $WO_3\text{-}MoO_3/ZrO_2$ and dealt with in the publications of "SHOKUBAI", "Chemistry Letters" and "Advances in Catalysis" and in "J Chem. Soc., Chem. Commun.", pp. 1059 to 1060 (1988) as well.

These super acids are obtained by depositing a compound of tungsten and/or molybdenum on zirconium hydroxide or amorphous zirconium oxide and then calcining the resultant composite in the atmosphere of an inert gas such as air or nitrogen gas at a temperature in the range of 500° to 1,000° C., preferably 650° to 850° C., for a period in the approximate range of 1 to 10 hours, preferably 2 to 8 hours.

The amount of tungsten oxide, molybdenum oxide, or tungsten-molybdenum composite oxide to be deposited is generally in the range of 1 to 40% by weight, preferably 3 to 40% by weight, based on the amount of zirconium oxide.

(6) Super acid of tungsten oxide/tin oxide titanium oxide, iron oxide, or composite oxide of at least two elements selected among tin, titanium, and iron:

These super acids are expressed as $WO_3/SnO_2$, $WO_3/TiO_2$, $WO_3/Fe_2O_3$, $WO_3/SnO_2\text{-}TiO_2$, $WO_3/SnO_2\text{-}Fe_2O_3$, $WO_3/TiO_2\text{-}Fe_2O_3$, and $WO_3/SnO_2\text{-}TiO_2\text{-}Fe_2O_3$ and dealt with in the publication of "SHOKUBAI" and in "Stud. Surf. Soc. Catal.", Vol. 75, pp. 2613 to 2616 (1953) as well.

These super acids are obtained by depositing a tungsten compound on at least one compound selected from the group consisting of stannic hydroxide, amorphous stannic oxide, titanium hydroxide, amorphous titanium oxide, ferric hydroxide, and amorphous ferric oxide and then calcining the resultant composite in the atmosphere of an inert gas such as air or nitrogen gas at a temperature in the range of 650° to 1,200° C. preferably 650° to 1,000° C. for a period in the approximate range of 1 to 10 hours, preferably 2 to 8 hours.

The amount of tungsten oxide to be carried is generally in the range of 1 to 40% by weight, preferably 3 to 40% by weight, based on the amount of the oxide such as tin oxide or titanium oxide.

(7) Super acid of phosphorus tungstate and/or an alkali metal salt thereof:

These super acids are expressed as $H_3P_1W_{12}O_{40}$ and $H_{3-x}A_xP_1W_{12}O_{40}$, [wherein A is an alkali metal (sodium, potassium, rubidium, and/or cesium) and x is above 0 and below 3 (0<x<3)]. These super acids are dealt with in "Chem. Tech.", November (1993), PP. 28 to 29.

These super acids are obtained by calcining phosphorus tungstate or alkali salts thereof in the atmosphere of an inert gas such as air or nitrogen gas at a temperature in the range of 350° to 500° C. preferably 380° to 450° C. for a period in the approximate range of 1 to 10 hours, preferably 2 to 8 hours.

As the component (B) according to this invention, two or more of the various super acids mentioned above may be used in a combined form.

Some of the solid acids to be used as the component (B) show degrees of acid strength of not more than −16.04 (Ho ≦−16.04). These degrees cannot be definitely determined, however, because no methods have yet been established for determining acid strength less than −16.04. The super acids (1) through (7) mentioned above invariably show degrees of acid strength of not more than −11.93 and, therefore, can be effectively used as the component (B) of this invention.

Acid Strength (Ho):

The acid strength in this invention has been determined by the following method which is now in general use.

When a color of a sample subjected to the determination is white, this sample is immersed in benzene and a benzene solution containing an acid-base indicator of a known pKa value is added thereto. The sample is kept under observation until the indicator on the surface of the sample assumes the color of acidity. The smallest value of pKa at which the color of acidity is assumed is reported as the acid strength of the sample.

The indicators (pKa) which are usable for this determination include m-nitrotoluene (−12.0), p-nitrotoluene (−12.4), p-nitrochlorobenzene (−12.7), m-nitroohlorobenzene (−13.2 ), 2,4-dinitrotoluene (−13.8), 2,4-dinitrofluorobenzene (−14.5 ), and 1,3,5-trinitrobenzene (−16.0), for example.

When a given sample has a color, the sample is first placed in a container provided with a gas inlet and a gas outlet line. Then the container holding the sample is evacuated until thorough expulsion of the entrapped air and ammonia gas is introduced into the container and adsorbed on the sample. Then, the ammonia gas is gradually discharged from the container and meanwhile the temperature of the container is gradually elevated. The ammonia gas discharged at a varying level of the temperature in the container is collected with liquefied nitrogen. The amount of ammonia thus collected is determined on the weight of the sample. By rating this amount with the aid of a calibration curve separately obtained with samples of known degrees of acid strength, the acid strength of the sample is calculated.

Catalyst

The catalyst of this invention contains the component (A) and the component (B) mentioned above. The amount of the component (B) based on the weight of the component (A) (as oxide) is generally in the range of 0.5 to 30% by weight, preferably 1 to 20% by weight. If the amount of the component (B) is less than 0.5% by weight, the effect of the addition of this component (B) will not be satisfactorily obtained. Conversely, if the amount exceeds 30% by weight, the activity of the catalyst will be found to decrease, the selectivity to unsaturated aldehyde and unsaturated carboxylic acid from isobutylene etc. will be unduly small, and the selectivity to $CO_2$ and CO will be unduly large. To be specific, when a component (B) is used singly, a reaction of forming $CO_2$ and CO is easily carried out because the conversion of isobutylene etc. and the selectivity to unsaturated aldehyde and unsaturated carboxylic acid are unduly low. The component (B), therefore, is a component to be disadvantageously used singly in the vapor-phase catalytic oxidation reaction according to this invention.

It, however, was demonstrated that by introducing a component (B) into a component (A), the activity and the selectivity to unsaturated aldehyde and unsaturated carboxylic acid from isobutylene etc. by the use of the component (A) are improved. Particularly when a component (B) is introduced into a component (A) in such a proportion as mentioned above, the component (B) can prominently manifest its effects as a cocatalyst.

The catalyst of this invention can be used all by itself. Optionally, it may be used as deposited on an inert carrier such as, for example, alumina, silica-alumina, silicon carbide, titanium oxide, magnesium oxide, or aluminum sponge. In this case, in the deposited catalyst may be incorporated such inorganic fibers as glass fibers or various whiskers which are widely known to permit effective improvement of the strength and the attrition loss of the catalyst. Further, for the purpose of controlling the physical properties of the catalyst with high repeatability, such additives as ammonium nitrate, cellulose, starch, polyvinyl alcohol, and stearic acid which are generally known as powder binders may be used.

The catalyst is not particularly discriminated on account of its shape. It may be in any desired shape such as, for example, pellets, beads, cylinders, rings, and tablets. The average diameter of the catalyst particles is generally in the range of 1 to 15 mm, preferably 3 to 10 mm.

The catalyst which contains the component (A) and the component (B) is not particularly discriminated on account of the method adopted for its preparation. It can be prepared by any desired method. For example, the method which comprises first preparing the components each in a powdery form and then mixing them homogeneously by the use of a ball mill and the method which comprises causing the component (B) prepared in advance to be dispersed in the component (A) at any desired stage during the preparation of the component (A) may be adopted.

Generally, after the component (A) and the component (B) have been thoroughly mixed, the resultant mixture optionally combined with water as a molding auxiliary is molded in a desired shape and the molded mixture is calcined under a stream of air at a temperature in the range of 300° to 600° C., preferably 350° to 550° C., for a period in the approximate range of 1 to 10 hours, preferably 2 to 8 hours. Thus, the catalyst is used in a molded form.

Vapor-phase catalytic oxidation:

The vapor-phase catalytic oxidation reaction according to this invention is not particularly discriminated on account of the apparatus and the operating conditions to be adopted. As respects the reaction conditions, the vapor-phase catalytic oxidation can be carried out under such conditions as are generally adopted for the production of unsaturated aldehyde and unsaturated carboxylic acid by the reaction mentioned above.

For example, a mixed gas comprising 1 to 10% by volume, preferably 2 to 8% by volume of at least one compound selected from the group consisting of propylene, isobutylene, t-butanol and methyl-t-butyl ether, 1 to 10 times, preferably 1 to 8 times its volume of the starting material gas of molecular oxygen and an inert gas such as nitrogen gas, carbon dioxide gas, and steam serving as a diluent (particularly, the use of steam is advantageous in repressing the formation of by-products and enhancing the yield of the product aimed at) is brought into contact with the catalyst of this invention at a temperature in the range of 250° to 450 ° C., preferably 280° to 420° C., under a pressure in the range of normal pressure to 10 atmospheres, preferably normal pressure to 8 atmospheres, at a space velocity in the range of 300 to 5,000 hr (STP), preferably 500 to 4,000 $hr^{-1}$(STP).

According to the method of this invention, as unsaturated aldehyde and unsaturated carboxylic acid, acrolein and acrylic acid can be obtained from propylene, methacrolein and methacrylic acid from isobutylene, methacrolein and methacrylic acid from t-butanol, and methacrolein and methacrylic acid from methyl-t-butyl ether, respectively.

Function:

The solid super acid which is highly effective in the acid catalytic reaction also manifests activity in the oxidation reaction. Indeed, the oxidation of butanes to CO and $CO_2$, the formation of acetaldehyde and acetone from ethylene, and the formation of cyclohexanone from cyclohexanol have been known to the art. Nevertheless, the fact that the solid super acid is also effective in the oxidation reaction resulting in the formation of unsaturated aldehyde and unsaturated carboxylic acid has never been known to date.

The function of the component (B) in the catalyst of this invention has not yet been fully elucidated. It is, however, inferred that the component (B) contributes to stabilize the composite oxide of the component (A) because the strong acidity of the component (B) promotes the adsorption of such reactive substances as propylene and isobutylene on the catalyst and consequently exalts the activity of the catalyst and further because the component (B) possesses a large surface area and moreover excels in resistance to heat. It should be noted, however, that this invention is not restricted by such theoretical consideration as mentioned above.

Now, this invention will be more specifically described below with reference to working examples. The terms "conversion", "total selectivity", and "total per pass yield" are defined as follows.

Conversion (%)

=[(Number of mols of raw material compound consumed in the reaction)/(Number of mols of raw material compound fed to the reaction)] (×100)

Total Selectivity (%)

=[(Number of mols of unsaturated aldehyde and unsaturated carboxylic acid formed)/(Number of mols of raw material compound consumed in the reaction)] (×100)

Total Per pass yield

=[(Number of mols of unsaturated aldehyde and unsaturated carboxylic acid formed)/(Number of mols of raw material compound fed to the reaction)] (×100)

EXAMPLE 1

Preparation of catalyst

Component (A)

In 1 liters of deionized water, 1,456 g of cobalt nitrate and 202 g of ferric nitrate were dissolved. Further, 243 g of bismuth nitrate was dissolved in an aqueous nitric acid solution comprising 30 ml of concentrated nitric acid and 120 ml of deionized water.

Separately, in 3 liters of heated deionized water, 1,059 g of ammonium paramolybdate and 265 g of ammonium paratungstate were placed and stirred until dissolution. Two kinds of aqueous solution separately prepared as described above were added dropwisely to the resultant aqueous solution and mixed. Then, in the resultant mixed solution, an aqueous solution having 39 g cesium nitrate dissolved in 200 ml of deionized water, and 203 g of silica sol with a concentration of 20% by weight were added sequentially and mixed therewith.

The slurry consequently obtained was heated and stirred, evaporated to dryness, and thereafter pulverized to obtain a molybdenum-tungsten-bismuth-iron type composite oxide powder (hereinafter referred to as "Powder (A-1)").

Component (B)

In deionized water, 250 g of zirconium oxynitrate was wholly dissolved. The solution was kept stirred and aqua ammonia was gradually added thereto to give rise to zirconium hydroxide. The formed zirconium hydroxide was separated by filtration, washed thoroughly with deionized water, and then dried at 100° C. for 24 hours. The dry hydroxide was spread on a funnel (filter paper) and sulfuric acid separately prepared at a concentration of 0.25 mol was caused to flow in 10 split portions on the spread hydroxide while kept suctioned so as to effect thorough expulsion of an excess of the sulfate ion-containing solution by aspiration. The hydroxide was dried and then calcined in a stream of air at 500° C. for three hours to obtain $SO_4/ZrO_2$ super acid powder having acid strength of −14.5 (hereinafter referred to as "Powder (B-1)").

A catalyst (1) was obtained by thoroughly mixing 1,699 g of the powder (A-1) (as oxide) with 62.5 g of the powder (B-1) (as oxide), molding the resultant mixture with water as a molding auxiliary to obtain pellets of 6 mm in outside diameter and 6.6 mm in length, drying the pellets, and calcining the dried pellets under a stream of air at 500° C. for 6 hours. The ratio of the powder (B-1) to the powder (A-1) (as oxide) was 3.7% by weight. The composition of elements of the catalyst (1) by atomic ratio (excluding oxygen; invariably applicable hereinafter) was as follows.

$$Mo_{12}W_2Bi_1Fe_1Co_{10}Cs_{0.4}Si_{1.35}-(Zr_{1.0}S_{0.02})$$

Oxidation reaction

A reaction vessel of steel of 25.4 mm in diameter was packed with 1,500 ml of the catalyst (1). A mixed gas having the composition comprising 6% by volume of isobutylene, 13.2% by volume of oxygen, 10% by volume of steam and 70.8% by volume of nitrogen gas was introduced into the reaction vessel and subjected to the oxidation reaction at a reaction temperature of 330° C. and a space velocity of 1,600 hr$^{-1}$ (STP). The results are as shown in Table 1.

Control 1

Preparation of catalyst

A catalyst (2) was prepared by following the procedure of Example 1 while using only the powder (A-1).

Oxidation reaction

The oxidation reaction was carried out by following the procedure of Example 1 while using the catalyst (2) in place of the catalyst (1) and changing the reaction temperature to 330° C. or 340° C. The results are as shown in Table 1.

Comparison of Example 1 and Control 1 reveals that the catalyst (1) of this invention excels the catalyst (2) for comparison in catalytic activity and exhibits the same degree of catalytic activity even at lower temperatures.

EXAMPLE 2

Preparation of catalyst

A catalyst (3) was obtained by following the procedure used for the preparation of the powder (A-1) in Example 1 while adding 62.5 g of the powder (B-1) (as oxide) to the slurry, heating and stirring the resultant mixture, and evaporating the mixture to dryness, molding the dry mixture with water as a molding auxiliary to obtain pellets of 6 mm in outside diameter and 6.6 mm in length, drying the pellets, and calcining the dried pellets under a stream of air at 500° C. for 6 hours. The composition of elements and the ratio of the powder (B-1) to the powder (A-1) (as oxide) of the catalyst (3) were as same as those of catalyst (1).

Oxidation reaction

The oxidation reaction was carried out by following the procedure of Example 1 while using the catalyst (3) in place of the catalyst (1). The results are as shown in Table 1.

EXAMPLE 3

Preparation of catalyst

A catalyst (4) was obtained by following the procedure used for the preparation of the powder (A-1) in Example 1 while preparatorily adding 62.5 g of the powder (B-1) (as oxide) to the deionized water having ammonium paramolybdate and ammonium paratungstate placed therein. The composition of elements and the ratio of the powder (B-1) to the powder (A-1) (as oxide) of the catalyst (4) were as same as those of catalyst (1).

Oxidation reaction

The oxidation reaction was carried out by following the procedure of Example 1 while using the catalyst (4) in place of the catalyst (1). The results are as shown in Table 1.

EXAMPLE 4

Oxidation reaction

The oxidation reaction using the catalyst (3) was continued for 4,000 hours in the same manner as in Example 2. The results after the reaction for 4,000 hours are shown in Table 1.

It is shown from the results of Table 1 that the deterioration level of the catalytic activity after the oxidation reaction for 4,000 hours was very small and that the decrease of the yield was also too low to be ignored. It, therefore, is clear that by using the catalyst (3), the extremely stable oxidation reaction can be continued over a long period.

Control 2

Oxidation reaction

The oxidation reaction was carried out by following the procedure of Control 1 while changing the reaction temperature to 340° C. and the reaction period to 4,000 hours. The results are as shown in Table 1.

Comparison of Control 1 (reaction temperature of 340° C.) and Control 2 reveals that the catalyst (2) for comparison is deficient in catalytic activity and causes the yield to decrease to a large extent after the reaction for a long time, and therefore, has a problem in stability.

EXAMPLE 5

Oxidation reaction

The oxidation reaction was carried out by following the procedure of Example 2 while changing the reaction temperature and space velocity to 360° C. and 3,000 hr⁻¹ respectively. The results are shown in Table 1.

Control 3

Oxidation reaction

The oxidation reaction was carried out by following the procedure of Example 5 while using the catalyst (2) instead of the catalyst (3). The results are as shown in Table 1.

Comparison of Example 5 and Control 3 reveals that the catalyst (3) of this invention excels the catalyst (2) for comparison both in catalytic activity and yield even under a high space velocity condition.

EXAMPLE 6

Oxidation reaction

The oxidation reaction was carried out by following the procedure of Example 2 while changing the proportions of isobutylene and nitrogen gas in the raw material gas to 7.0% by volume and 69.8% by volume respectively. The results are shown in Table 1.

Control 4

Oxidation reaction

The oxidation reaction was carried out by following the procedure of Example 6 while using the catalyst (2) instead of the catalyst (3). The results are as shown in Table 1.

Comparison of Example 6 and Control 4 reveals that that the catalyst (3) of this invention excels the catalyst (2) for comparison both in catalytic activity and yield even when the concentration of isobutylene in the raw material gas is increased.

TABLE 1

| | Catalyst No. | Reaction temperature (°C.) | Conversion of isobuty-lene (mol %) | Total selectivity (mol %) | Total per pass yield (mol %) |
|---|---|---|---|---|---|
| Example 1 | (1) | 330 | 98.5 | 88.2 | 86.9 |
| Control 1 | (2) | 330 | 96.5 | 88.1 | 85.0 |
| | | 340 | 98.3 | 87.9 | 86.4 |
| Example 2 | (3) | 330 | 98.7 | 88.0 | 86.9 |
| Example 3 | (4) | 330 | 99.0 | 87.8 | 86.9 |
| Example 4 | (3) | 330 | 98.2 | 88.4 | 86.8 |
| Control 2 | (2) | 340 | 95.1 | 88.0 | 83.7 |
| Example 5 | (3) | 360 | 98.6 | 88.4 | 87.2 |
| Control 3 | (2) | 360 | 95.9 | 87.6 | 84.0 |
| Example 6 | (3) | 330 | 98.9 | 87.6 | 86.6 |
| Control 4 | (2) | 330 | 96.7 | 87.4 | 84.5 |

EXAMPLE 7

Oxidation reaction

The oxidation reaction was carried out by following the procedure of Example 2 while using t-butanol as a raw material gas in place of isobutylene. The results are shown in Table 2.

Control 5

Oxidation reaction

The oxidation reaction was carried out by following the procedure of Example 7 while using the catalyst (2) in place of the catalyst (3). The results are as shown in Table 2.

TABLE 2

| | Catalyst No. | Reaction temperature (°C.) | Conversion of t-buta-nol (mol %) | Total selectivity (mol %) | Total per pass yield (mol %) |
|---|---|---|---|---|---|
| Example 7 | (3) | 330 | 100 | 87.1 | 87.1 |
| Control 5 | (2) | 330 | 100 | 85.0 | 85.0 |

EXAMPLE 8

Oxidation reaction

The oxidation reaction was carried out by following the procedure of Example 2 while using a mixed gas comprising 5% by volume of methyl-t-butyl ether (MTBE), 13.2% by volume of oxygen, 10% by volume of steam and 71.8% by volume of nitrogen gas, and changing the space velocity and reaction temperature to 1,000 hr⁻¹ and 360° C. respectively. The results are shown in Table 3.

Control 6

Oxidation reaction

The oxidation reaction was carried out by following the procedure of Example 8 while using the catalyst (2) in place of the catalyst (3). The results are as shown in Table 3.

TABLE 3

| | Catalyst No. | Reaction temperature (°C.) | Conversion of MTBE (mol %) | Total selectivity (mol %) | Total per pass yield (mol %) |
|---|---|---|---|---|---|
| Example 8 | (3) | 360 | 99.0 | 86.5 | 85.6 |
| Control 6 | (2) | 360 | 97.1 | 86.4 | 83.9 |

MTBE: methyl-t-butyl ether

EXAMPLE 9

Preparation of catalyst

A catalyst (5) was prepared by following the procedure of Example 2 while changing the ratio of the powder (B-1) to the powder (A-1) added (as oxide) to 7.4% by weight. The composition of elements of this catalyst (5) by atomic ratio was as follows.

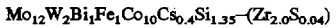

$$Mo_{12}W_2Bi_1Fe_1Co_{10}Cs_{0.4}Si_{1.35}-(Zr_{2.0}S_{0.04})$$

Oxidation reaction

The oxidation reaction was carried out by following the procedure of Example 1 while using the catalyst (5) in place of the catalyst (1). The results are as shown in Table 4.

EXAMPLE 10

Preparation of catalyst

A SO₄/TiO₂ super acid powder having acid strength of −13.8 (hereinafter referred to as "Powder (B-10)") was prepared by following the procedure for the preparation of the powder (B-1) in Example 1 while using titanium tetrachloride in place of zirconium oxychloride and changing the calcination temperature to 520° C. Then, a catalyst (6) was prepared by following the procedure of Example 2 while using the powder (B-10) in place of the powder (B-1). The ratio of the powder (B-10) to the powder (A-1) (as oxide) was 2.4% by weight. The composition of elements of this catalyst (6) in atomic ratio was as follows.

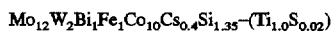

$$Mo_{12}W_2Bi_1Fe_1Co_{10}Cs_{0.4}Si_{1.35}\text{—}(Ti_{1.0}S_{0.02})$$

Oxidation reaction

An oxidation reaction was carried out by following the procedure of Example I while using the catalyst (6) in place of the catalyst (1). The results are as shown in Table 4.

EXAMPLE 11

Preparation of catalyst

A $SO_4/SnO_2$ super acid powder having acid strength of −14.5 (hereinafter referred to as "Powder (B-11)") was prepared by following the procedure used for the preparation of the powder (B-1) in Example 1 while using stannic chloride in place of zirconium oxychloride and changing the calcination temperature to 550° C. Then, a catalyst (7) was prepared by following the procedure of Example 2 while using the powder (B-11) in place of the powder (B-1). The ratio of the powder (B-11) to the powder (A-1) (as oxide) was 4.5% by weight. The composition of elements of this catalyst (7) in atomic ratio was as follows.

$$Mo_{12}W_2Bi_1Fe_1Co_{10}Cs_{0.4}Si_{1.35}\text{—}(Sn_{1.0}S_{0.02})$$

Oxidation reaction

An oxidation reaction was carried out by following the procedure Of Example 1 while using the catalyst (7) in place of the catalyst (1). The results are as shown in Table 4.

EXAMPLE 12

Preparation of catalyst

A $SO_4/HfO_2$ super acid powder having acid strength of −13.2 (hereinafter referred to as "Powder (B-12)") was prepared by following the procedure used for the preparation of the powder (B-1) in Example 1 while using hafnium chloride in place of zirconium oxychloride and changing the calcination temperature to 650° C. Then, a catalyst (8) was prepared by following the procedure of Example 2 while using the powder (B-12) in place of the powder (B-1). The ratio of the powder (B-12) to the powder (A-1) (as oxide) was 6.2% by weight. The composition of elements of this catalyst (8) in atomic ratio was as follows.

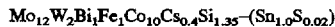

$$Mo_{12}W_2Bi_1Fe_1Co_{10}Cs_{0.4}Si_{1.35}\text{—}(Hf_{1.0}S_{0.02})$$

Oxidation reaction

An oxidation reaction was carried out by following the procedure of Example 1 while using the catalyst (8) in place of the catalyst (1). The results are as shown in Table 4.

EXAMPLE 13

Preparation of catalyst

A $SO_4/Fe_2O_3$ super acid powder having acid strength of −12.7 (hereinafter referred to as "Powder (B-13)") was prepared by following the procedure used for the preparation of the powder (B-1) in Example 1 while using iron chloride in place of zirconium oxychloride. Then, a catalyst (9) was prepared by following the procedure of Example 2 while using the powder (B-13) in place of the powder (B-1). The ratio of the powder (B-13) to the powder (A-1) (as oxide) was 2.4% by weight. The composition of elements of this catalyst (9) in atomic ratio was as shown below.

$$Mo_{12}W_2Bi_1Fe_1Co_{10}Cs_{0.4}Si_{1.35}\text{—}(Fe_1S_{0.01})$$

Oxidation reaction

An oxidation reaction was carried out by following the procedure of Example 1 while using the catalyst (9) in place of the catalyst (1). The results are as shown in Table 4.

EXAMPLE 14

Preparation of catalyst

Silica gel was obtained by dissolving 100 g of ethyl silicate in deionized water, adding several drops of concentrated nitric acid to the resultant solution, and stirring the mixture. This silica gel was dried at 100° C., then immersed in $SO_2Cl_2$, and calcined at 400° C. to obtain a $SO_4/SiO_2$ super acid powder having acid strength of −12.7 (hereinafter referred to as "Powder (B-14)"). Then, a catalyst (10) was prepared by following the procedure of Example 2 while using the powder (B-14) in place of the powder (B-1). The ratio of the powder (B-14) to the powder (A-1) (as oxide) was 1.8% by weight. The composition of elements of this catalyst (10) in atomic ratio was as shown below.

$$Mo_{12}W_2Bi_1Fe_1Co_{10}Cs_{0.4}Si_{1.35}\text{—}(Si_{1.0}S_{0.02})$$

Oxidation reaction

An oxidation reaction was carried out by following the procedure of Example 1 while using the catalyst (10) in place of the catalyst (1). The results are as shown in Table 4.

EXAMPLE 15

Preparation of catalyst

A $SO_4/Al_2O_3$ super acid powder having acid strength of −13.8 (hereinafter referred to as "Powder (B-15)") was obtained by combining y-alumina with 5N sulfuric acid and calcining the resultant mixture at 600° C. Then, a catalyst (11) was prepared by following the procedure of Example 2 while using the powder (B-15) in place of the powder (B-1). The ratio of the powder (B-15) to the powder (A-1) (as oxide) was 1.6% by weight. The composition of elements of this catalyst (11) in atomic ratio was as follows.

$$Mo_{12}W_2Bi_1Fe_1Co_{10}Cs_{0.4}Si_{1.35}\text{—}(Al_{1.0}S_{0.02})$$

Oxidation reaction

An oxidation reaction was carried out by following the procedure of Example 1 while using the catalyst (11) in place of the catalyst (1). The results are as shown in Table 4.

EXAMPLE 16

Preparation of catalyst

A $WO_3/ZrO_2$ super acid powder having acid strength of −13.8 (hereinafter referred to as "Powder (B-16)") was prepared by following the procedure used for the preparation of the powder (B-1) in Example 1 while using an aqueous solution of ammonium metatungstate in place of the aqueous sulfuric acid solution. Then, a catalyst (12) was prepared by following the procedure of Example 2 while using the powder (B-16) in place of the powder (B-1). The ratio of the powder (B-16) to the powder (A-1) (as oxide) was 4.6% by weight. The composition of elements of this catalyst (12) in atomic ratio was as shown below. The amount of $WO_3$ deposited on $ZrO_2$ was 28.2% by weight.

$$Mo_{12}W_2Bi_1Fe_1Co_{10}Cs_{0.4}Si_{1.35}-(Zr_{1.0}W_{0.15})$$

Oxidation reaction

An oxidation reaction was carried out by following the procedure of Example 1 while using the catalyst (12) in place of the catalyst (1). The results are as shown in Table 4.

EXAMPLE 17

Preparation of catalyst

A $MoO_3/ZrO_2$ super acid powder having acid strength of −12.7 (hereinafter referred to as "Powder (B-17)") was prepared by following the procedure of Example 16 while using an aqueous solution of ammonium paramolybdate in place of the aqueous solution of ammonium metatungstate. Then, a catalyst (13) was prepared by following the procedure of Example 2 while using the powder (B-17) in place of the powder (B-1). The ratio of the powder (B-17) to the powder (A-1) (as oxide) was 4.0% by weight. The composition of elements of this catalyst (13) in atomic ratio was as shown below. The amount of $MoO_3$ deposited on $ZrO_2$ was 11.7% by weight.

$$Mo_{12}W_2Bi_1Fe_1Co_{10}Cs_{0.4}Si_{1.35}-(Zr_{1.0}Mo_{0.10})$$

Oxidation reaction

An oxidation reaction was carried out by following the procedure of Example 1 while using the catalyst (13) in place of the catalyst (1). The results are as shown in Table 4.

EXAMPLE 18

Preparation of catalyst

A $WO_3/SnO_2$ super acid powder having acid strength of −12.0 (hereinafter referred to as "Powder (B-18)") was prepared by following the procedure used for the preparation of the powder (B-1) in Example 1 while using dry tin hydroxide in place of dry zirconium hydroxide and an aqueous solution of ammonium metatungstate in place of the aqueous solution of sulfuric acid and changing the calcination temperature to 900° C. Then, a catalyst (14) was prepared by following the procedure of Example 2 while using the powder (B-18) in place of the powder (B-1). The ratio of the powder (B-18) to the powder (A-1) (as oxide) was 5.3% by weight. The composition of elements of this catalyst (14) in atomic ratio was as follows. The amount of $WO_3$ deposited on $SnO_2$ was 20.0% by weight.

$$Mo_{12}W_2Bi_1Fe_1Co_{10}Cs_{0.4}Si_{1.35}-(Sn_{1.0}W_{0.13})$$

Oxidation reaction

An oxidation reaction was carried out by following the procedure of Example 1 while using the catalyst (14) in place of the catalyst (1). The results are as shown in Table 4.

EXAMPLE 19

Preparation of catalyst

A $WO_3/TiO_2$ super acid powder having acid strength of −12.4 (hereinafter referred to as "Powder (B-19)") was prepared by following the procedure used for the preparation of the powder (B-18) in Example 18 while using dry titanium hydroxide in place of dry tin hydroxide and changing the calcination temperature to 700° C. Then, a catalyst (15) was prepared by following the procedure of Example 2 while using the powder (B-19) in place of the powder (B-1). The ratio of the powder (B-19) to the powder (A-1) (as oxide) was 3.1% by weight. The composition of elements of this catalyst (15) in atomic ratio was as follows. The amount of $WO_3$ deposited on $TiO_2$ was 31.9% by weight.

$$Mo_{12}W_2Bi_1Fe_1Co_{10}Cs_{0.4}Si_{1.35}-(Ti_{1.0}W_{0.11})$$

Oxidation reaction

An oxidation reaction was carried out by following the procedure of Example 1 while using the catalyst (15) in place of the catalyst (1). The results are as shown in Table 4.

EXAMPLE 20

Preparation of catalyst

A $WO_3/Fe_2O_3$ super acid powder having acid strength of −12.0 (hereinafter referred to as "Powder (B-20)") was prepared by following the procedure used for the preparation of the powder (B-18) in Example 18 while using dry iron hydroxide in place of dry tin hydroxide and changing the calcination temperature to 700° C. Then, a catalyst (16) was prepared by following the procedure of Example 2 while using the powder (B-20) in place of the powder (B-1). The ratio of the powder (B-20) to the powder (A-1) (as oxide) was 3.2% by weight. The composition of elements of this catalyst (16) in atomic ratio was as shown below. The amount of $WO_3$ deposited on $Fe_2O_3$ was 37.8% by weight.

$$Mo_{12}W_2Bi_1Fe_1Co_{10}Cs_{0.4}Si_{1.35}-(Fe_{1.0}W_{0.13})$$

Oxidation reaction

An oxidation reaction was carried out by following the procedure of Example 1 while using the catalyst (16) in place of the catalyst (1). The results are as shown in Table 4.

EXAMPLE 21

Preparation of catalyst

A compound of the following composition (excluding oxygen) was prepared by dissolving phosphorus tungstate in deionized water and adding the resultant solution to an aqueous solution obtained in advance by dissolving cesium nitrate in deionized water.

$$Cs_{2.5}H_{0.5}P_1W_{12}$$

A cesium phosphorus tungstate super acid powder having acid strength of −12.4 (hereinafter referred to as "Powder (B-21)") was obtained by calcining the resultant compound at 400° C. Then, a catalyst (17) was prepared by following the procedure of Example 2 while using the powder (B-21) in place of the powder (B-1). The ratio of the powder (B-21) to the powder (A-1) (as oxide) was 18.9% by weight. The composition of elements of this catalyst (17) in atomic ratio was as follows.

$$Mo_{12}W_2Bi_1Fe_1Co_{10}Cs_{0.4}Si_{1.35}-(Cs_{2.5}H_{0.5}P_1W_{12})_{0.2}$$

Oxidation reaction

An oxidation reaction was carried out by following the procedure of Example 1 while using the catalyst (17) in place of the catalyst (1). The results are as shown in Table 4.

EXAMPLE 22

Preparation of catalyst

A molybdenum-tungsten-bismuth-iron type composite oxide powder (hereinafter referred to as "Powder (A-22)") was prepared by following the procedure used for the preparation of the powder (A-1) in Example 1 while using nickel nitrate in place of cobalt nitrate, adding further phosphoric acid after the addition of ammonium paratungstate, using rubidium nitrate in place of cesium nitrate, adding further stannic oxide after the addition of rubidium nitrate, and using aluminum nitrate in place of silica sol.

A catalyst (18) was obtained in the same manner as in Example 1 except for thoroughly mixing the powder (A-22) with the powder (B-1) obtained in Example 1. The ratio of the powder (B-1) to the powder (A-22) (as oxide) was 3.4% by weight. The composition of elements of this catalyst (18) in atomic ratio was as shown below.

$$Mo_{12}W_2Bi_3Fe_1Ni_7Rb_1P_{0.2}Sn_{0.5}Al_1-(Zr_{1.0}S_{0.02})$$

Oxidation reaction

An oxidation reaction was carried out by following the procedure of Example 1 while using the catalyst (18) in place of the catalyst (1). The results are as shown in Table 4.

Control 7

Preparation of catalyst

A catalyst (19) was prepared by following the procedure of Example 22 while using the powder (A-22) exclusively.

Oxidation reaction

An oxidation reaction was carried out by following the procedure of Example 22 while using the catalyst (19) in place of the catalyst (18). The results are as shown in Table 4.

EXAMPLE 23

Preparation of catalyst

A molybdenum-bismuth-iron type composite oxide powder (hereinafter referred to as "Powder (A-23)") was prepared by following the procedure used for the preparation of the powder (A-1) in Example 1 while omitting the use of ammonium paratungstate, placing potassium nitrate, lithium nitrate, magnesium nitrate and calcium nitrate in place of cesium nitrate, using titanium dioxide in place of silica sol, and further using cerous nitrate and niobium pentoxide in the final process.

A catalyst (20) was obtained in the same manner as in Example 1 except for thoroughly mixing the powder (A-23) with the powder (B-1) obtained in Example 1. The ratio of the powder (B-1) to the powder (A-23) (as oxide) was 4.0% by weight. The composition of elements of this catalyst (20) in atomic ratio was as shown below.

$$Mo_{12}Bi_1Fe_1Co_{10}K_{0.5}Li_{0.2}Ca_{0.2}Mg_{0.2}Nb_{0.5}Ce_1Ti_1-(Zr_{1.0}S_{0.02})$$

Oxidation reaction

An oxidation reaction was carried out by following the procedure of Example 1 while using the catalyst (20) in place of the catalyst (1) and changing the reaction temperature to 340° C. The results are as shown in Table 4.

Control 8

Preparation of catalyst

A catalyst (21) was prepared by following the procedure of Example 23 while using the powder (A-23) exclusively.

Oxidation reaction

An oxidation reaction was carried out by following the procedure of Example 23 while using the catalyst (21) in place of the catalyst (20). The results are as shown in Table 4.

EXAMPLE 24

Preparation of catalyst

A molybdenum-bismuth-iron type composite oxide powder (hereinafter referred to as "Powder (A-24)") was prepared by following the procedure used for the preparation of the powder (A-1) in Example 1 while omitting the use of ammonium paratungstate, placing thallium nitrate and strontium nitrate in place of cesium nitrate and thereafter adding tellurium oxide, lead nitrate and zinc nitrate thereto, and using titanium dioxide in place of silica sol.

A catalyst (22) was obtained in the same manner as in Example 1 except for thoroughly mixing the powder (A-24) with the powder (B-1) obtained in Example 1. The ratio of the powder (B-1) to the powder (A-24) (as oxide) was 3.8% by weight. The composition of elements of this catalyst (22) in atomic ratio was as shown below.

$$Mo_{12}Bi_1Fe_3Co_7Tl_{0.7}Sr_{0.3}Te_{0.3}Pb_1Zn_{0.5}Ti_1-(Zr_{1.0}S_{0.02})$$

Oxidation reaction

An oxidation reaction was carried out by following the procedure of Example 1 while using the catalyst (22) in place of the catalyst (1) and changing the reaction temperature to 340° C. The results are as shown in Table 4.

Control 9

Preparation of catalyst

A catalyst (23) was prepared by following the procedure of Example 24 while using the powder (A-24) exclusively.

Oxidation reaction

An oxidation reaction was carried out by following the procedure of Example 24 while using the catalyst (23) in place of the catalyst (22). The results are as shown in Table 4.

EXAMPLE 25

Preparation of catalyst

A molybdenum-tungsten-bismuth-iron type composite oxide powder (hereinafter referred to as "Powder (A-25)") was prepared by following the procedure used for the preparation of the powder (A-1) in Example 1 while using potassium nitrate, barium nitrate and beryllium nitrate in place of cesium nitrate and thereafter adding antimony trioxide and manganese nitrate thereto, and using zirconium nitrate in place of silica sol.

A catalyst (24) was obtained in the same manner is in Example 1 except for thoroughly mixing the powder (A-25) with the powder (B-1) obtained in Example 1. The ratio of the powder (B-1) to the powder (A-25) (as oxide) was 3.9% by weight. The composition of elements of this catalyst (24) in atomic ratio was as shown below.

$$Mo_{12}W_{1.5}Bi_1Fe_{1.2}Co_5K_{1.0}Ba_{0.2}Be_{0.2}Sb_1Mn_{0.5}Zr_1-(Zr_{1.0}S_{0.02})$$

Oxidation reaction

An oxidation reaction was carried out by following the procedure of Example 1 while using the catalyst (24) in place of the catalyst (1). The results are as shown in Table 4.

Control 10

Preparation of catalyst

A catalyst (25) was prepared by following the procedure of Example 25 while using the powder (A-25) exclusively.

Oxidation reaction

An oxidation reaction was carried out by following the procedure of Example 25 while using the catalyst (25) in place of the catalyst (24). The results are as shown in Table 4.

TABLE 4

| | Catalyst No. | Reaction temperature (°C.) | Conversion of isobutylene (mol %) | Total selectivity (mol %) | Total per pass yield (mol %) |
|---|---|---|---|---|---|
| Example 9 | (5) | 330 | 98.8 | 87.8 | 86.7 |
| Example 10 | (6) | 330 | 97.5 | 88.3 | 86.1 |
| Example 11 | (7) | 330 | 98.3 | 88.2 | 86.7 |
| Example 12 | (8) | 330 | 97.3 | 87.7 | 85.3 |
| Example 13 | (9) | 330 | 97.5 | 88.0 | 85.8 |
| Example 14 | (10) | 330 | 97.5 | 88.0 | 85.8 |
| Example 15 | (11) | 330 | 97.7 | 88.1 | 86.1 |
| Example 16 | (12) | 330 | 97.4 | 88.0 | 85.7 |
| Example 17 | (13) | 330 | 97.0 | 88.2 | 85.6 |
| Example 18 | (14) | 330 | 96.8 | 88.2 | 85.4 |
| Example 19 | (15) | 330 | 97.0 | 87.9 | 85.3 |
| Example 20 | (16) | 330 | 96.7 | 88.1 | 85.2 |
| Example 21 | (17) | 330 | 96.4 | 87.8 | 84.6 |
| Example 22 | (18) | 330 | 97.9 | 87.1 | 85.3 |
| Control 7 | (19) | 330 | 95.7 | 87.0 | 83.3 |
| Example 23 | (20) | 340 | 98.3 | 85.1 | 83.6 |
| Control 8 | (21) | 340 | 96.1 | 85.2 | 81.9 |
| Example 24 | (22) | 340 | 98.2 | 87.1 | 85.5 |
| Control 9 | (23) | 340 | 96.3 | 87.1 | 83.9 |
| Example 25 | (24) | 330 | 97.5 | 85.0 | 82.9 |
| Control 10 | (25) | 330 | 95.3 | 85.3 | 81.3 |

EXAMPLE 26

Preparation of catalyst

A composite oxide powder (hereinafter referred to as "Powder (A-26)") having the elemental composition (atomic ratio) as described below was prepared in the same manner as in Example 1.

$$Mo_{12}W_2Bi_1Fe_1Co_4K_{0.06}Si_{1.35}$$

A catalyst (26) was obtained by thoroughly mixing this powder (A-26) with the powder (B-1) obtained in Example 1, molding the resultant mixture to obtain pellets of 6 mm in outside diameter and 6.6 mm in length, and calcining the pellets under a stream of air at 450° C. for 6 hours. The ratio of the powder (B-1) to the powder (A-26) (as oxide) was 4.3% by weight. The composition of elements of the catalyst (26) by atomic ratio was as follows.

$$Mo_{12}W_2Bi_1Fe_1Co_4K_{0.06}Si_{1.35}-(Zr_{1.0}S_{0.02})$$

Oxidation reaction

The reaction vessel as used in Example 1 was packed with 1,500 ml of the catalyst (26). A mixed gas having the composition comprising 6% by volume of propylene, 12% by volume of oxygen, 10% by volume of steam and 72% by volume of nitrogen gas was introduced into the reaction vessel and subjected to the oxidation reaction at a reaction temperature of 300° C. and a space velocity of 2,000 hr$^{-1}$. As the result, the conversion of propylene was 98.5%, the total selectivity to acrolein and acrylic acid and total per pass yield were 94.0% and 92.6%, respectively.

Control 11

Preparation of catalyst

A catalyst (27) was prepared by following the procedure of Example 26 while omitting the addition of the powder (B-1).

Oxidation reaction

An oxidation reaction was carried out by following the procedure of Example 26 while using the catalyst (27) in place of the catalyst (26). As the result, the conversion of propylene was 95.0%, the total selectivity to acrolein and acrylic acid and total per pass yield were 93.8% and 89.1%, respectively.

What is claimed is:

1. A catalyst for producing unsaturated aldehyde and unsaturated carboxylic acid by the oxidation of at least one compound selected from the group consisting of propylene, isobutylene, t-butanol and methyl-t-butyl ether in a vapor phase with molecular oxygen or a molecular oxygen-containing gas, comprising (A) a composite oxide represented by the following general formula (1):

$$Mo_aW_bBi_cFe_dA_eB_fC_gD_hE_iO_x \qquad (1)$$

wherein Mo is molybdenum, W is tungsten, Bi is bismuth, Fe is iron, A is at least one element selected from the group consisting of nickel and cobalt, B is at least one element selected from the group consisting of alkali metals and thallium, C is at least one alkaline earth metal, D is at least one element selected from the group consisting of phosphorus, tellurium, antimony, tin, cerium, lead, niobium, manganese, arsenic and zinc, E is at least one element selected from the group consisting of silicon, aluminum, titanium end zirconium, and O is oxygen, and a, b, c, d, e, f, g, h, i, and x are atomic ratios respectively of Mo, W, Bl, Fe, A, B, C, D, E, and O such that b is a numeral in the range of 0.5 to 10, c in the range of 0.1 to 10, d in the range of 0.1 to 20, e in the range of 2 to 20, f in the range of 0 to 4 in the range of 0 to 30, and x is a numeral to be determined by the oxidized states of the elements when a is fixed at 12 and (B) a solid acid having acid strength (Ho) of not more than −11.93 (Ho $\leq$ −11.93) wherein the ratio of said component (B) to said component (A) (as oxide) is in the range of 0.5 to 30% by weight.

2. The catalyst according to claim 1, wherein said component (B) is a super acid of $SO_4$/oxide of a metal of Group IV in the Periodic Table of Elements.

3. The catalyst according to claim 2, wherein said metal of Group IV in the Periodic Table of Elements is at least one member selected from the group consisting of zirconium, titanium, tin, and hafnium.

4. The catalyst according to claim 1, wherein said component (B) is a $SO_4$/iron oxide super acid.

5. The catalyst according to claim 1, wherein said component (B) is a $SO_4$/silicon oxide super acid.

6. The catalyst according to claim 1, wherein said component (B) is a $SO_4$/aluminum oxide super acid.

7. The catalyst according to claim 1, wherein said component (B) is a tungsten oxide, molybdenum oxide, or tungsten-molybdenum composite oxide/zirconium oxide super acid.

8. The catalyst according to claim 1, wherein said component (B) is a super acid of tungsten oxide/tin oxide, titanium oxide, iron oxide, or composite oxide of at least two elements selected among tin, titanium, and iron.

9. The catalyst according to claim 1, wherein said component (B) is a super acid of phosphorus tungstate and/or an alkali metal salt thereof.

10. A method for the production of unsaturated aldehyde and unsaturated carboxylic acid by the vapor-phase catalytic oxidation reaction of at least one compound selected from the group consisting of propylene, isobutylene, t-butanol and methyl-t-butyl ether in a vapor phase with molecular oxygen or a molecular oxygen-containing gas, which method comprises effecting said reaction in the presence of the catalyst for the production of unsaturated aldehyde and unsaturated carboxylic acid set forth in any of claim 1.

* * * * *